United States Patent [19]
Lee et al.

[11] Patent Number: 5,840,968
[45] Date of Patent: Nov. 24, 1998

[54] METHOD AND APPARATUS FOR PREPARING PURIFIED TEREPHTHALIC ACID

[75] Inventors: Fu-Ming Lee; Wiston Lamshing, both of Katy, Tex.

[73] Assignee: HFM International, Inc., Houston, Tex.

[21] Appl. No.: 962,030

[22] Filed: Oct. 31, 1997

Related U.S. Application Data

[63] Continuation-in-part of Ser. No. 760,890, Dec. 6, 1996, which is a continuation-in-part of Ser. No. 477,898, Jun. 7, 1995, Pat. No. 5,767,311.

[51] Int. Cl.[6] ........................................... C07C 51/42
[52] U.S. Cl. ........................................... 562/486; 562/486
[58] Field of Search ..................... 562/485, 486

[56] References Cited

U.S. PATENT DOCUMENTS

| | | | |
|---|---|---|---|
| 5,159,109 | 10/1992 | Rosen et al. | 562/486 |
| 5,344,969 | 9/1994 | Iwane et al. | 562/486 |

*Primary Examiner*—Samuel Barts
*Attorney, Agent, or Firm*—Jenkens & Gilchrist, P.C.

[57] ABSTRACT

A method and apparatus for purifying crude terephthalic acid from a liquid dispersion thereof also containing impurities selected from unreacted starting materials, solvents, products of side reactions and/or other undesired materials is provided. The method comprises the steps of filtering the dispersion to form a crude terephthalic acid filter cake, dissolving the filter cake in a selective crystallization solvent at an elevated temperature to form a solution, crystallizing purified terephthalic acid from the solution in the crystallization solvent by reducing the pressure and temperature of the solution, and separating the crystallized purified terephthalic acid from the solution. According to the invention, the selective crystallization solvent is non-aqueous, non-corrosive and essentially non-reactive with terephthalic acid. Preferably, the selective crystallization solvent is N-methyl pyrrolidone or dimethyl acetamide. The method and apparatus produces purified terephthalic acid having a purity desired for use in forming polyester resin and other products at an economically attractive rate and at operating conditions of reduced severity which require a lower capital investment and simplified processing.

31 Claims, 6 Drawing Sheets

METHOD AND APPARATUS FOR PREPARING PURIFIED TEREPHTHALIC ACID

This application is a continuation-in-part of application Ser. No. 08/760,890, filed Dec. 6, 1996, entitled Method and Apparatus for Preparing Purified Terephthalic Acid, which is in turn a continuation-in-part of application Serial No. 08/477,898, filed Jun. 7, 1995, now U.S. Pat. No. 5,767,311 entitled Method and Apparatus for Preparing Purified Terephthalic Acid, both of which are assigned to the same assignee as this application, and the totality of the disclosures of which are hereby incorporated by reference for all purposes.

The present invention relates to a method and apparatus for preparing purified terephthalic acid. It also relates to methods and apparatuses for purifying crude terephthalic acid to produce a purified terephthalic acid product which is a useful starting material for producing polyester resin, which is in turn useful for the production of fibers, film, plastic bottles, and polyester resin structures, often reinforced by other materials such as glass fiber.

BACKGROUND OF THE INVENTION

Purified terephthalic acid (PTA) is a starting material for the formation of polyester resin, which is, in turn, used to make many materials of commerce having a variety of utilities. Purified terephthalic acid is formed from "crude" terephthalic acid conventionally by a number of purification methods, often with the aid of catalysts. The methods for purifying crude terephthalic acid heretofore available are not completely satisfactory either from an engineering standpoint, or from an economic standpoint, yet the purity of the purified terephthalic acid is an important determinant of the satisfactoriness of the processes by which the polyester resin is formed.

A number of reaction systems are known for forming crude terephthalic acid from a variety of starting materials. The purification aspects of the present invention may be used with substantially any of these reaction systems, but in accordance with the invention it is preferred that a reaction system involving the oxidation of paraxylene (p-xylene) be employed, and the use of such a synthesis system forms a part of the present invention.

The problems of existing and prior systems for producing purified terephthalic acid center around the difficulties in running the reaction systems to produce good yields of crude terephthalic acid economically, compounded by the difficulties of refining the crude terephthalic acid to eliminate impurities and unwanted components to produce purified terephthalic acid of a quality suitable as a starting material for producing polyester. Concomitant problems in prior systems include the high capital investment required for PTA plants, the severity of operating conditions of prior processes, both for the production of crude terephthalic acid, and for its purification, and the need for handling catalyst systems and reaction solvents, as well as reaction byproducts in a way such that environmental problems are minimized, and loss of material is also controlled.

One factor of importance in the production of purified terephthalic acid is the formation of crystals having a size and shape giving them good handling characteristics, washability and filterability in the PTA manufacturing process, and easier handling and better processability in the polyester process.

SUMMARY OF THE INVENTION

In accordance with the present invention there is provided a method and apparatus for producing purified terephthalic acid. In one aspect, the method includes the production of crude terephthalic acid by the oxidation of p-xylene. The oxidation step produces not only terephthalic acid, but p-toluic acid and 4-carboxybenzaldehyde (4-CBA) as oxidation intermediates and other impurities from side reactions. The product produced in the oxidation step is a liquid dispersion containing unreacted starting materials, solvents, if any have been used, oxidation intermediate products, particularly those just mentioned, and other materials which are not desired in the sought-for purified terephthalic acid. The oxidation step of the present invention is so conducted that the conversion to crude terephthalic acid should be at least about 30% by weight per pass of p-xylene.

In further accordance with the invention, the crude terephthalic acid from the oxidizer is first grossly separated from the other materials from the oxidizer and then it is re-dissolved in a selective crystallization solvent and, optionally, one or more additional solvents of the invention discussed below. The re-dissolved crude terephthalic acid is then crystallized out of the selective crystallization solvent and additional solvents of the invention in one or, preferably, two crystallization stages. Provision is made to separate out the crystallized and progressively purified terephthalic acid from the solvents of the invention, and the filter cake of purified terephthalic acid ultimately obtained is washed with other solvents of the invention and dried or, alternatively, dried (e.g., using a vacuum dryer), sent to a soaker to remove residual solvent, and ultimately filtered and dried for storage or for further processing.

Also in accordance with the present invention, any crude TA produced by existing and prior oxidation systems may be purified. An important advantage of the present invention is that it can process a higher content of oxidation intermediates, like 4-CBA, making it possible to relax oxidation conditions, which reduces p-xylene and acetic acid burning losses.

Also in accordance with the present invention, improvements in the crystallization processes just outlined are provided which produce larger, globular crystals that are thought to contain little or no salt of the kind which may tend to form when the selective crystallization solvent(s) is an organic base. The larger non-salt crystals have the advantage that they resist destruction by water rinsing and are otherwise easier to recover solvent from, as well as being easier to rinse for removal of residual impurities.

The improvements in the crystallization processes comprise flashing solvent from the crystallizing acid by reducing the pressure on it, preferably both prior to and during the cooling of the saturated acid solution. It is further preferred to reduce the pressure progressively to lower levels, either in a batch or continuous flow crystallizer, and this may be arranged to be performed stepwise or continuously. Still further, heat may be added to the crystallizing acid during the application of reduced pressure to increase the rate and quantity of solvent removal, care being taken, however, to avoid materially increasing the temperature of the crystallizing acid to cause redissolution of the acid and consequent waste of energy.

As was mentioned above, in accordance with the invention, crystallization may be performed in multiple stages; when this form of the invention is used, it is preferred that some or all of the crystallization improvement techniques just discussed be utilized in the second or last stage, although the techniques may also be used to advantage in the first stage.

Further in accordance with the invention, co-solvents may be used for purifying terephthalic acid by flash crystallization. A co-solvent having a lower boiling point than the solvent can be used to reduce the flashing temperature for crystallization and hence the dissolution temperature. With a lower flashing temperature, crystallization can be carried out under a lower degree of vacuum.

The co-solvents include water, $C_1$ to $C_5$ alcohols, such as methanol or ethanol, $C_5$ to $C_{10}$ hydrocarbons, such as p-xylene, and $C_1$ to $C_{10}$ organic acids, such as formic acid or acetic acid, etc. It is thus possible to include about 1 to about 50% inert solvents having boiling points ranging from 25° to 200° C. as the co-solvents.

The invention also contemplates that steps are included to reclaim and recycle the solvents of the invention at each stage of crystallization and washing, including recycle of some of the recovered materials to the oxidizer. Steps are also taken to closely control the delivery of any objectionable materials to the environment.

In an important aspect, the present invention is based on several discoveries relating to solvents which are effective to bring about the purification of crude terephthalic acid through crystallization and separation steps. These discoveries may be summarized in several ways as follows.

The selective crystallization solvents useful in the practice of the present invention include those in which (a) the impurities desired to be separated from terephthalic acid to purify it are relatively more soluble in the solvent than is the terephthalic acid at substantially every temperature within the desired range of temperatures at which the solvent containing terephthalic acid is to be handled, and (b) the terephthalic acid is more soluble at an elevated temperature and less soluble at a lower or reduced temperature. It is to be understood that the term "selective crystallization solvent" is intended to mean solvents useful in the selective crystallization of terephthalic acid as described above and as described in greater detail below and as shown in FIGS. 1 and 2.

In this connection it should be noted that U.S. Pat. No. 3,465,035 mentions that certain organic solvents (pyridine, dimethyl sulfoxides, dimethyl foramide, and the like) have been used to purify terephthalic acid, but that they suffer from being unstable in air and easily form addition products with terephthalic acid. This same patent, along with several others, also teaches the use of acetic acid and water as purification solvents for terephthalic acid. By contrast, the selective crystallization solvents according to the present invention are (a) non-aqueous, (b) non-corrosive, and (c) essentially non-reactive with terephthalic acid and do not include those prior practices just described. Specifically, water, acetic (and other alkyl) acid, and the above-mentioned organic solvents are excluded from the selective crystallization solvents which are contemplated by the present invention.

In accordance with the invention, the primary preferred selective crystallization solvents are N-methyl pyrrolidone (NMP) and N,N-dimethyl acetamide (DMAC), for the several reasons discussed below, and for their superior performance. U.S. Pat. No. 2,949,483, dated Aug. 16, 1960 to Ham, discloses NMP used to crystallize terephthalic acid, but does not use the same crystallization temperature range as is preferred in the present invention. Nor does it suggest flash crystallization or its advantageous results. Tr. Vses. Nauch.-Issled. Proekt. Inst. Monomerov (1970), 2(2), 26–32; From: Ref. Zh., Khim. 1971, Abstr. No. 1N166; V. N. Kulakov, et al.; entitled "Purification of Aromatic Dicarboxylic Acids Obtained by Liquid-Phase Oxidation of Dialkyl Derivatives of Aromatic Hydrocarbons," very briefly mentions NMP as a solvent, but says nothing about dissolution or crystallization temperatures or flash crystallization.

N-methyl pyrrolidone (NMP) and N,N-dimethyl acetamide (DMAC) are the preferred selective crystallization solvents for the practice of the invention. These solvents are non-aqueous, thermally stable, non-toxic (environmentally safe), noncorrosive, and commercially available. NMP is the most preferred selective crystallization solvent for the practice of the present invention, because its solubility versus temperature curve for terephthalic acid slopes upwardly and to the right, which means that terephthalic acid can be dissolved in it at elevated temperatures, and precipitated or crystallized from it at lower temperatures.

Although NMP is the most preferred selective crystallization solvent, it is to be understood that DMAC exhibits similar desirable characteristics and that, in accordance with the present invention, other preferred selective crystallization solvents for purification of crude terephthalic acid can be selected from various polar organic solvents including, but not intended to be limited to, N-alkyl-2-pyrrolidone (such as N-ethyl pyrrolidone), N-mercaptoalkyl-2-pyrrolidone (such as N-mercaptoethyl-2-pyrrolidone), N-alkyl-2-thiopyrrolidone (such as N-methyl-2-thiopyrrolidone), and N-hydroxyalkyl-2-pyrrolidone (such as N-hydroxyethyl-2-pyrrolidone), 1,5-dimethyl pyrrolidone, N-methyl piperidone, N-methyl caprolactam, N,N-dimethyl formamide, and N-formyl piperidine, and the like, and mixtures thereof. Still other selective crystallization solvents contemplated by the present invention include, but are not intended to be limited to, sulfolane, methyl sulfolane, the sulfones, the morpholines (such as, morpholine and N-formyl morpholine), the carbitols, $C^1$ to $C^{12}$ alcohols, the ethers, the amines, the amides, and the esters, and the like, and mixtures thereof.

It is preferred that the desired selective crystallization solvent be used in a multi-stage crystallization process in combination with one or more additional solvents, preferably two such additional solvents, particularly where the crude terephthalic acid is less than about 98% pure. Preferably, a wash solvent, such as, but not intended to be limited to, water, p-xylene, acetone, methyl ethyl ketone (MEK) or methanol, and the like, is used in the washing of the initial filter cake obtained from the first separation of crude terephthalic acid from other materials issuing from the oxidizer. In addition, a displacement solvent having a low boiling point, such as, but not intended to be limited to, water, methanol, acetone, MEK, and the like, may be used. Preferably, water is used as the displacement solvent in association with the third filter following the second crystallization stage in the preferred process. The desired displacement solvent displaces the selective crystallization solvent from the resulting filter cake, whereby substantially only the displacement solvent is present during the soaking process. The soaking process is preferred to eliminate any possible residual solvent trapped in the TA crystals before the product is subjected to the final filtration and drying steps.

As described above, NMP and DMAC are the preferred selective crystallization solvents for the practice of the invention. They are non-aqueous, thermally stable, non-toxic (environmentally safe), non-corrosive, and commercially available. NMP is a preferred selective crystallization solvent for the practice of the present invention, because, among other things, its solubility versus temperature curve for terephthalic acid slopes upwardly and to the right, which means that terephthalic acid can be dissolved in it at elevated temperatures, and precipitated or crystallized from it at lower temperatures. However, the solubility versus temperature curve for terephthalic acid is of a much milder slope than the solubility curves in NMP for other materials sought to be separated from crude terephthalic acid, such as benzoic acid, 4-carboxybenzaldehyde (4-CBA), and p-toluic acid. As a consequence, when crude terephthalic acid, containing or associated with unreacted starting materials, solvents (if any), and oxidation intermediate products, such as those mentioned above, or other undesired materials, is dissolved in NMP or DMAC at an elevated temperature, substantially all the materials are dissolved or at least highly dispersed. Then upon removal of heat and pressure and subsequent cooling of the NMP or DMAC solution of such dissolved materials, the pure terephthalic acid preferentially crystallizes out, while the other more soluble materials which may be regarded as impurities for the present purposes remain in solution in NMP or DMAC. A separation is thus effected between purified terephthalic acid and its associated impurities. NMP or DMAC may be stripped of the impurities in a reclaiming column and recycled into the process, while the impurities may be recycled to the oxidizer step or otherwise disposed of.

In accordance with a preferred form of the invention, a method is provided for purifying crude terephthalic acid from a liquid dispersion thereof also containing impurities selected from unreacted starting materials, solvents, products of side reactions and/or other undesired materials. It includes preparing first stage purified terephthalic acid from said crude terephthalic acid and redissolving the first stage purified terephthalic acid in a selective crystallization solvent to form a solution. Second stage purified terephthalic acid is crystallized from the solution by reducing the temperature and pressure sufficient to flash evaporate solvent from the terephthalic acid of the solution but without cooling the solution below about 50° C. Second stage purified terephthalic acid is then separated from the solution, and the separated second stage purified terephthalic acid is washed with water. The washed separated second stage purified terephthalic acid is soaked in water between about 150° C. and about 300 ° C., preferably between about 180° C. and about 250° C., and the water soaked second stage purified terephthalic acid is then filtered and dried.

If desired, the terephthalic solution is held from about 15 to about 60 minutes, preferably about 20 to about 40 minutes, following the reduction of temperature and prior to separating the second stage purified terephthalic acid therefrom. Also, the washing of purified terephthalic acid may be done between one and three times. Similarly, the operation of reducing the temperature and pressure to flash evaporate solvent may be performed stage-wise, in from two to six stages, preferably two to four stages. Advantageously, the proportion of solvent flash evaporated in the first evaporation stage is restricted to increase final crystal size.

In further accordance with the invention, a method is provided for purifying crude terephthalic acid from a liquid dispersion thereof also containing impurities selected from unreacted starting materials, solvents, products of side reactions and/or other undesired materials. The method includes filtering the dispersion to form a crude terephthalic acid filter cake, dissolving the filter cake in a selective crystallization solvent at a temperature above about 60° C. to form a solution, crystallizing purified terephthalic acid from the solution by reducing the temperature and/or pressure of said solution but not below about 50° C., separating said crystallized purified terephthalic acid from the solution, washing the separated purified terephthalic acid with water, soaking the washed separated purified terephthalic acid with water at about 150°–300° C., preferably between 180°–250° C., and filtering and drying the water soaked purified terephthalic acid.

In accordance with another aspect of the invention, a method is provided for purifying crude terephthalic acid from a liquid dispersion thereof also containing impurities selected from unreacted starting materials, solvents, products of side reactions and/or other undesired materials which includes filtering the dispersion to form a crude terephthalic acid filter cake, dissolving the filter cake in a selective crystallization solvent at a temperature above about 50° C. to form a solution, crystallizing purified terephthalic acid from the solution by reducing the temperature and/or pressure thereof, separating the crystallized purified terephthalic acid from the solution, redissolving the separated purified terephthalic acid in a selective crystallization solvent to form a second solution, crystallizing second stage purified terephthalic acid from the second solution by reducing the temperature and pressure sufficient to flash evaporate solvent from the terephthalic acid of the second solution but without cooling that solution below about 50° C., and separating the second stage purified terephthalic acid from the second solution.

Still another embodiment of the invention includes a method for purifying crude terephthalic acid from a liquid dispersion thereof also containing impurities selected from unreacted starting materials, solvents, products of side reactions and/or other undesired materials by filtering the dispersion to form a crude terephthalic acid filter cake, dissolving the filter cake in a selective crystallization solvent at a temperature above about 50° C. to form a solution, crystallizing purified terephthalic acid from the solution by reducing the temperature and/or pressure thereof, separating the crystallized purified terephthalic acid from the solution, redissolving the separated purified terephthalic acid in a selective crystallization solvent to form a second solution, crystallizing second stage purified terephthalic acid from the second solution by reducing the temperature and pressure sufficient to flash evaporate solvent from the terephthalic acid of the second solution but without cooling said solution below about 50° C., separating the second stage purified terephthalic acid from the second solution, washing the separated second stage purified terephthalic acid with water, soaking the washed separated second stage purified terephthalic acid with water at about 150°–300° C., preferably between 180°–250° C., and filtering and drying the water soaked second stage purified terephthalic acid.

From the foregoing, it can be seen that an object of the present invention to provide an improved method and apparatus for producing purified terephthalic acid of a purity desired for use in forming polyester resin and other products, at an economically attractive rate, and at operating conditions of reduced severity which require a lower capital investment and simplified processing. The manner in which these and other objects of the invention are attained may be learned by consideration of the detailed description of the invention which follows, together with the accompanying drawings.

BRIEF DESCRIPTION OF THE DRAWINGS

A more complete understanding of the method and apparatus of the present invention may be obtained by reference to the following Detailed Description when taken in conjunction with the accompanying Drawings wherein.

DETAILED DESCRIPTION OF EMBODIMENTS

I. Process Description

Figure 1:
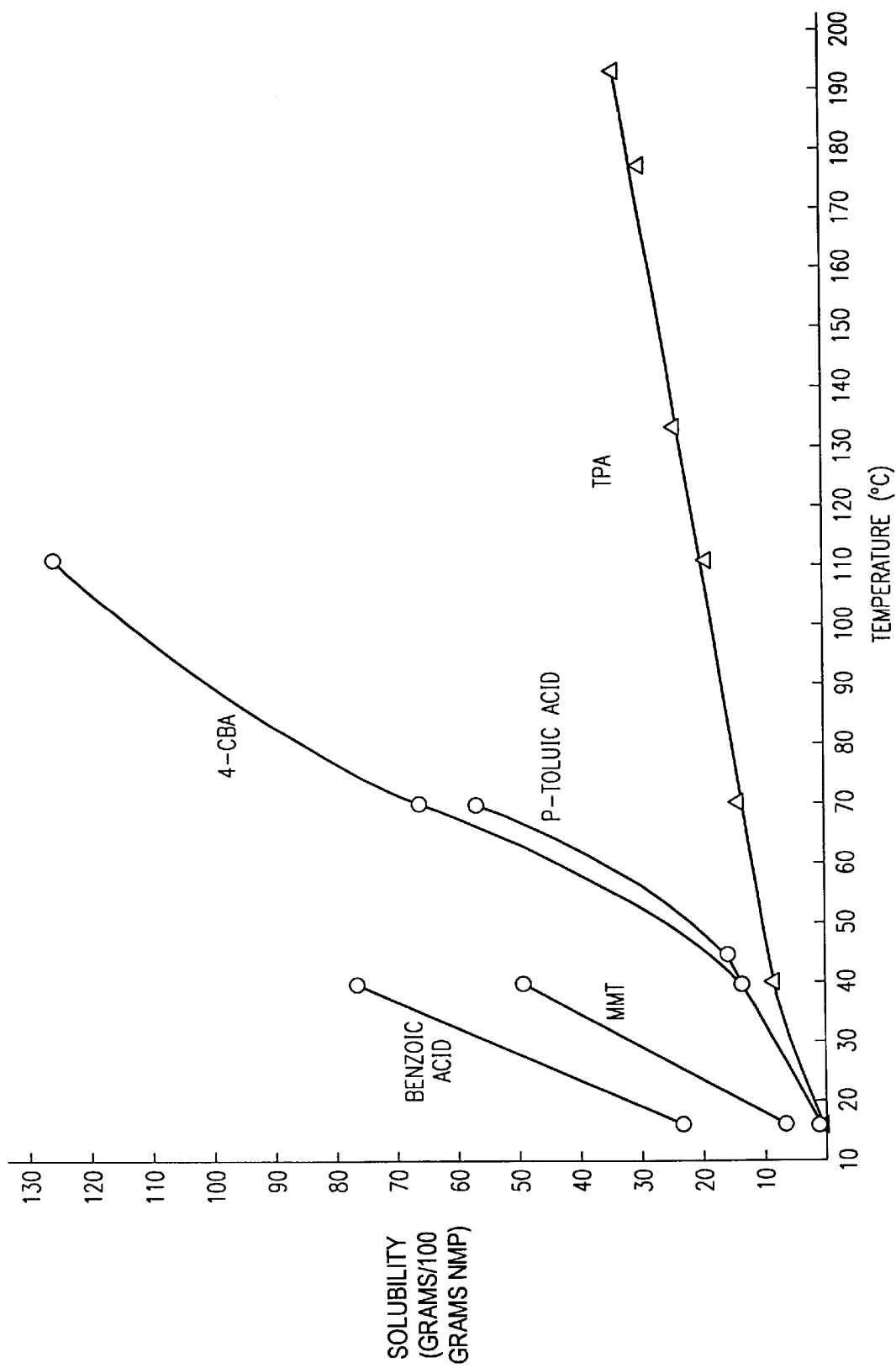
FIGS. 1 and 2 are plots of solubility versus temperature curves for terephthalic acid and for impurities or side reaction products commonly associated with crude terephthalic acid in NMP and DMAC, respectively.
Figure 2:
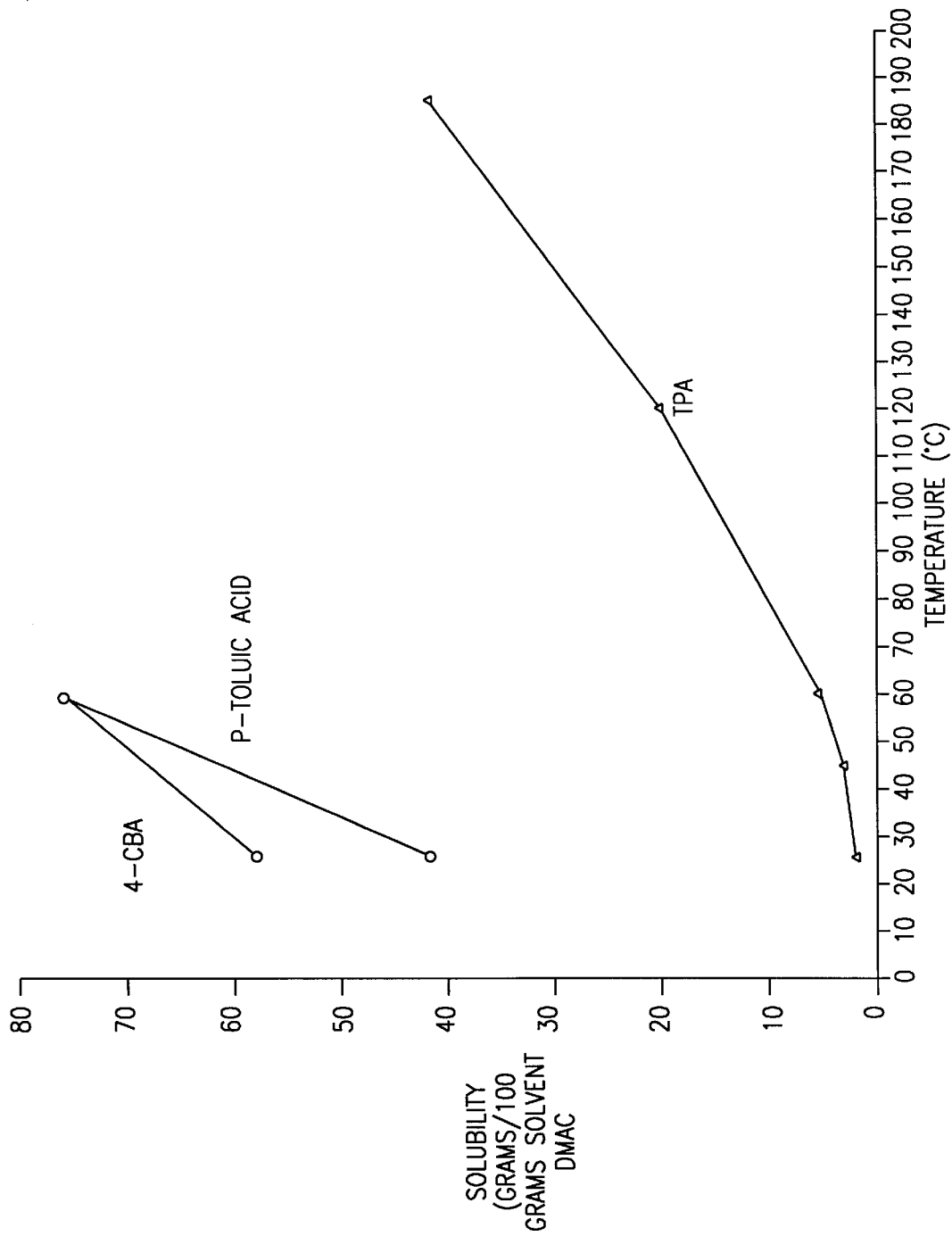

The present invention relates to the development of a new PTA manufacturing technology. Compared to the current widely used PTA technology, this technology provides a lower capital investment in new PTA plant construction, as well as lower costs of plant operation. It also provides means for current DMT plants to co-produce PTA, to strengthen their competitiveness against newer PTA plants.

Process Summary

The success of this process is based on the development of a low pressure, low temperature, non-aqueous, highly selective crystallization technology. The crystallization technology can purify the crude terephthalic acid (TA) with purity as low as from between about 70% (from the oxidizer) to about 98+% in the first-stage crystallizer, and to about 99.99+% in the second-stage crystallizer. This allows the TA oxidizer to be operated at much lower severity than those of widely used prior art processes. The selective crystallization solvent used in the crystallization process is non-aqueous, thermally stable, non-toxic (environmentally safe), non-corrosive, and commercially available.

When carrying out the method according to the present invention, employing NMP or DMAC as the selective crystallization solvent, the present inventors have demonstrated TA purity levels of up to 99.9+ wt % after a first crystallization process, and up to 99.99+ wt % after a second crystallization process. In particular, Table 1 illustrates the recovery of 99.95 wt % pure TA after the first crystallization process and 99.997 wt % pure TA after the second crystallization process, from crude TA (89.89 wt % TA).

TABLE 1

|  | 1st Crystallization | 2nd Crystallization |
|---|---|---|
| (a) Weight of TA: | 56.34 grams | 31.81 grams |
| (b) Weight of Crystallization Solvent (NMP): | 400.02 grams | 248.38 grams |
| (c) Saturation Temperature: | 60° C. | |
| (d) Crystallization Temperature: | 15° C. (one hour) | |
| (1) Crude TA Product Composition: | | |

| Benzoic | p-Toluic | 4-CBA | TA | Others |
|---|---|---|---|---|
| 0.39wt% | 4.49wt% | 2.49WT% | 89.89WT% | 274WT% |

TABLE 1-continued

|  | 1st Crystallization | | | 2nd Crystallization | |
|---|---|---|---|---|---|
| (2) First Crystallization Product | | | | | |
| 35ppm | 143ppm | 359ppm | 99.95wt% | | Not Detected |
| (3) Second Crystallization Product | | | | | |
| <20ppm | <20ppm | <10ppm | 99.997+wt% | | |

Table 2 illustrates the recovery of 99.90 wt % pure TA after the first crystallization process and 99.9933 wt % pure TA after the second crystallization process from crude TA (89.89 wt % TA) by increasing both the saturation temperature and the crystallization temperature.

TABLE 2

|  | 1st Crystallization | 2nd Crystallization |
|---|---|---|
| (a) Weight of TA: | 138.08 grams | 70.15 grams |
| (b) Weight of Crystallization Solvent (NMP): | 685.30 grams | 247.46 grams |
| (c) Saturation Temperature: | 110° C. | 105° C. |
| (d) Crystallization Temperature: | 40° C. | 40° C. |
| (1) Crude TA Product Composition: | | |

| Benzoic | p-Toluic | 4-CBA | TA | Others |
|---|---|---|---|---|
| 0.39wt% | 4.49wt% | 2.49wt% | 89.89wt% | 2.74wt% |

(2) First Crystallization Product (Recovery: 56.5wt%)

| Benzoic | p-Toluic | 4-CBA | TA | Others |
|---|---|---|---|---|
| 28ppm | 367ppm | 390ppm | 99.90wt% | 229ppm |

(3) Second Crystallization Product (Recovery: 47.5 wt%)

| <10ppm | <19ppm | 25ppm | 99.9933wt% | 13ppm |

Table 3 illustrates the recovery of 99.9960 wt % pure TA (single crystallization process) from crude TA (98.99 wt % TA). In addition, each of benzoic, p-Toluic, 4-CBA, MMT and other impurities were at less than 10 ppm.

TABLE 3

| (a) Weight of TA: | 152.67 grams |
|---|---|
| (b) Weight of Crystallization Solvent (NMP): | 786.19 grams |
| (c) Saturation Temperature: | 100° C. |
| (d) Crystallization Temperature: | 40° C. |

(1) Crude TA Product Composition:

| Benzoic | p-Toluic | 4-CBA | TA | MMT | Others |
|---|---|---|---|---|---|
| <10ppm | <10ppm | 18ppm | 98.99wt% | 303ppm | 0.98wt% |

(2) Crystallization Product (Recovery: 50.2 wt%)

| <10ppm | <10ppm | <10ppm | >99.9960wt% | <10ppm | <10ppm |

Table 4 illustrates the recovery of 99.63 wt % pure TA (single crystallization process) from crude TA (83.91 wt % TA) on a large scale basis.

TABLE 4

| (a) Weight of TA: | 1760 grams |
|---|---|
| (b) Weight of Crystallization Solvent (NMP): | 6162 grams |
| (c) Saturation Temperature: | 160° C. |
| (d) Crystallization Temperature: | 50° C. |

(1) Crude TA Feed Product Composition:

| Benzoic | p-Toluic | 4-CBA | TA | Others |
|---|---|---|---|---|
| 1.03wt% | 4.79wt% | 5.03wt% | 83.91wt% | 5.24wt% |

TABLE 4-continued (2) Crystallization Product (Recovery: 24.3wt%)

| 38ppm | 852ppm | 0.23wt% | 99.63wt% | 500ppm |

Table 5 illustrates the recovery of 99.92 wt % pure TA (single crystallization process) from crude TA (79.79 wt % TA) on a large scale basis.

TABLE 5

| | |
|---|---|
| (a) Weight of TA: | 1700 grams |
| (b) Weight of Crystallization Solvent (NMP): | 5928 grams |
| (c) Saturation Temperature: | 160° C. |
| (d) Crystallization Temperature: | 45° C. |

(1) Crude TA Feed Product Composition:

| Benzoic | p-Toluic | 4-CBA | TA | Others |
|---|---|---|---|---|
| 1.59wt% | 5.19wt% | 7.61wt% | 79.79wt% | 5.81wt% |

(2) Crystallization Product (Recovery: 31.5wt%)

| 10ppm | 203ppm | 446ppm | 99.92wt% | 184ppm |

Table 6 illustrates the recovery of 99.15 wt % pure TA (single crystallization process) from crude TA (83.90 wt % TA) on a large scale basis at a higher saturation temperature of 190° C.

TABLE 6

| | |
|---|---|
| (a) Weight of TA: | 965 grams |
| (b) Weight of Crystallization Solvent (NMP): | 5684 grams |
| (c) Saturation Temperature: | 190° C. |
| (d) Crystallization Temperature: | 40° C. |

(1) Crude TA Feed Product Composition:

| Benzoic | p-Toluic | 4-CBA | TA | Others |
|---|---|---|---|---|
| 1.23wt% | 5.25wt% | 6.34wt% | 83.90wt% | 3.28wt% |

(2) Crystallization Product (Recovery: 48.9wt%)

| — | 0.14wt% | 0.61wt% | 99.15wt% | 0.1wt% |

Table 7 illustrates the recovery of 99.9915 wt % pure TA from crude TA (98.50 wt % TA) on a large scale basis. The supersaturation of the crystallization mixture resulted in the formation of substantially larger TA crystals than those crystals resulting from the processes summarized above. As would be understood by one skilled in the art, the sizes of TA crystals are an important consideration with respect to separation thereof from solvents and impurities.

TABLE 7

| | |
|---|---|
| (a) Weight of TA: | 2333 grams |
| (b) Weight of Crystallization Solvent (NMP): | 5698 grams |
| (c) Saturation Temperature: | 160° C. |
| (d) Crystallization Temperature: | 45° C. |

(1) Crude TA Feed Product Composition:

| Benzoic | p-Toluic | 4-CBA | TA | Others |
|---|---|---|---|---|
| 198ppm | 0.15wt% | 1.23wt% | 98.50wt% | 989ppm |

(2) Crystallization Product (Recovery: 69.7wt%)

| <10ppm | 26ppm | 38ppm | 99.9915wt% | 11ppm |

Table 8 demonstrates the recovery of 99.45 wt % pure TPA (single crystallization process) from crude TPA (82.92 wt % TPA), using N,N-dimethyl acetamide (DMAC) as the crystallization solvent. The 4-CBA content was reduced from 6 wt % to 3276 ppm. The range of the operating temperature was very moderate (from 45° to 120° C.).

TABLE 8

Purifying "TPA" with N,N-Dimethyl Acetamide by Crystallization

1. 
| | |
|---|---|
| N,N-dimethylacetamide used: | 1,000.0 grams |
| Crude TPA used: | 291.5 grams |
| N,N-dimethylacetamide for cake wash: | 800 ml |
| Purified TPA recovered: | 135.6 grams (not including losses due to solids handling and sampling) |

| Sample | Benzoic | PTA | 4-CBA | TPA | Others |
|---|---|---|---|---|---|
| Crude TPA (wt%) | 5.25 | 6.01 | 4.59 | 82.92 | 1.23 |
| Purified TPA (ppm) | 689 | 3276 | 1519 | 99.45* | 13 |

*weight percent

2. Method:

(a) The mixture was heated to 120° C. in an agitated and jacketed flask to dissolve the solids, and the mixture was held at the temperature for one hour.
(b) The mixture was then cooled to 45° C. in one hour.
(c) The cooled slurry was then filtered in a separatory funnel under vacuum to separate the mother liquor from the cake.
(d) The cake was washed once in the separatory funnel with the solvent to remove the residual mother liquor in the cake. The wash was carried out at room temperature.
(e) The wet solid was soaked over night with D.I. water at room temperature and then washed three times with D.I. water in a separatory funnel.
(f) The solids were dried over night at 180° C.

Although for many purposes relatively high dissolution temperatures are preferred, i.e. 140° C.–200° C., experiments run at relatively low temperatures with cooling crystallization showed that similar purification may be achieved compared to complete dissolution at high temperature (160° C. or higher):

Experiment A:

| | |
|---|---|
| (a) Weigh of TA: | 254g |
| (b) Weigh of Crystallization Solvent: | 507g |
| (c) Initial ("saturation") Temperature: | 60° C. |
| (d) Crystallization Temperature: | 45° C. |

(1) Crude TA Composition:

| Benzoic | p-Toluic | 4-CBA | TA |
|---|---|---|---|
| 210ppm | 459ppm | 0.78% | 99.15% |

(2) Crystallization Product (Recovery 89.5%)

| 21ppm | 21ppm | 548ppm | 99.94% |

Experiment B:

| | |
|---|---|
| (a) Weigh of TA: | 256g |
| (b) Weigh of Crystallization Solvent: | 510g |
| (c) Initial ("saturation") Temperature: | 58° C. |
| (d) Crystallization Temperature: | 45° C. |

(1) Crude TA Composition:

| Benzoic | p-Toluic | 4-CBA | TA: | Others: |
|---|---|---|---|---|
| 0.27% | 5.3% | 2.53% | 91.56% | 0.34% |

(2) Crystallization Product (Recovery: 74.5%):

| 140ppm | 0.18% | 0.13% | 99.67% | 31ppm |

The use of lower dissolution temperatures may make possible economies in energy consumption in the process.

As has been discussed, important aspects of this invention are related to the discovery of methods to crystallize terephthalic acid (TA) from organic solution where the solvent tends to form an organic salt with TA. The salt is normally formed from cooling the solution of an organic solvent or a mixture of organic solvents, which solution is saturated with TA at higher temperatures. However, the crystal structure of the salt is destroyed when it is washed with water or other solvents to remove the solvent in the crystal. The washed crystals become very fine powders which are very difficult to filter and wash in order to remove the impurities in the trapped mother liquor and the residual solvent. Avoidance of such fine powders is desirable.

As is known, organic solvents easily form addition products with terephthalic acid with the result that difficulties are encountered in the purification and in recovering pure terephthalic acid. Some of these difficulties can be appreciated from an integration of various empirical observations. Salt crystals tend to be desirably large (>120–150 microns) but they are destroyed by contact with water, methanol or acetic acid (otherwise desirable washing agents) and are resolved into very fine crystals (<50 microns), which, as pointed out above, are difficult to handle. Cake formed from salt crystals is soft and easy to filter, but after water addition, the cake shrinks (its thickness is reduced), becoming a very compact cake that is very difficult to de-water and rinse for residual solvent removal. If an attempt is made to overcome this undesirable result by reslurrying the cake after water addition (at room temperature), it is found that a high viscosity paste forms instead of a slurry, unless solids concentration is held very low (<20%). The paste is difficult to process further. When reslurrying with hot water (60° C. or higher) is attempted, it is found that the mix has a high tendency to form a very stable foam (like shaving foam), which is also very difficult to process. Because of the small particle size resulting after water addition to salt crystals, the settling characteristics are very poor, and processing rates through the wash column are very low, requiring very big equipment. Notwithstanding the foregoing difficulties encountered in attempting to rinse residual solvent away from salt crystals, residual solvent removal still remains critical because such solvent can discolor TPA when heated to temperatures of 120° C. or higher. This will affect the quality of polyester made from such material. In addition, regeneration or water wash is needed in order to recover the solvent for reasons of cost.

Figure 3:
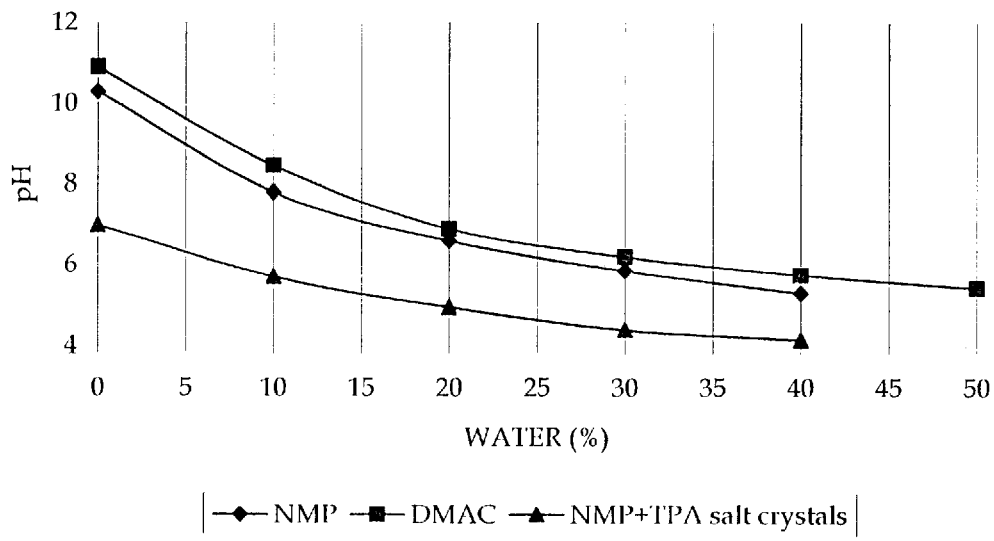
FIG. 3 is a plot of pH versus water concentration for NMP, DMAC, and NMP plus salt crystals.

Salt crystals can be visually differentiated from TPA crystals because the former are bright, transparent and slightly pale and the latter are opaque and whiter. Prior workers have reported that the salt contains 2 moles of solvent for each mol of TPA, which means that the salt formula is TPA:2NMP. Based on the weight formula, TPA is 45% and NMP is 55% in the salt. Empirically, it has been found that the solvent content of the salt crystals is confined between 55–65%, which confirms that the salt formula postulated by prior workers is correct and the difference is free solvent as moisture in the cake.

pH measurements at room temperature of NMP and DMAC indicate both solvents are basic (pH is 10.3 and 11 respectively). When TPA is added, pH drops to neutral, and when water is added, the mixture becomes acidic. FIG. 3 is a plot of pH versus water concentration for NMP, DMAC, and NMP plus TPA salt crystals.

Figure 4:
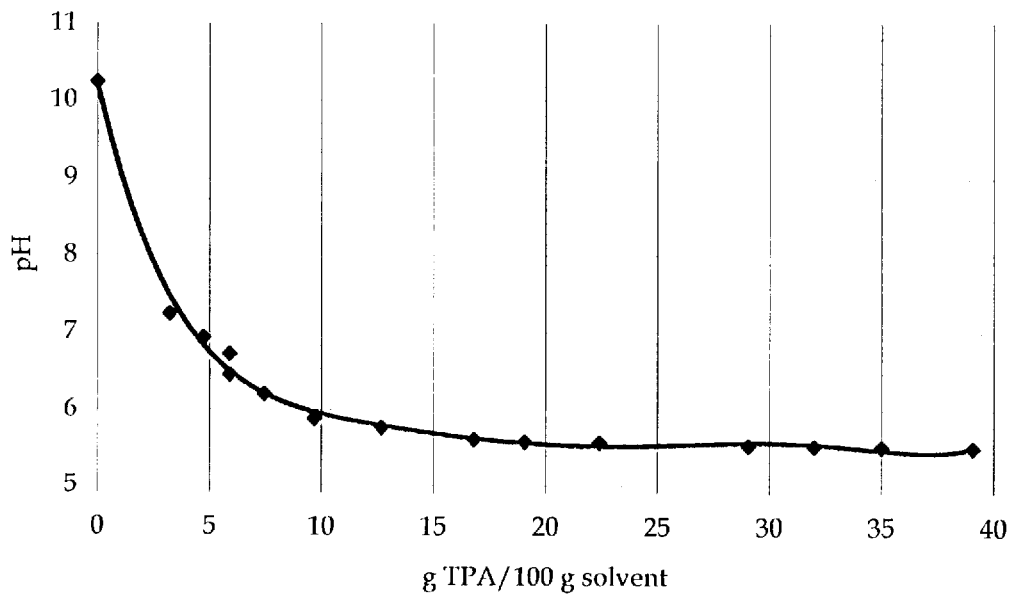
FIG. 4 is a plot of pH versus TPA/solvent weight ratio.

A study of the pH of different TPA-to-solvent mixtures at 30° C. showed the same type of behavior, going from basic to acidic as the proportion of TPA is increased. Around pH of 6.5, TPA starts precipitating, which means solution is saturated. FIG. 4 is a plot of pH versus TPA/solvent weight ratio.

The TPA used for pH measurements was a commercial PTA product (globular crystals) and the precipitated crystals were bars and transparent (salt crystals) which indicates that the original TPA crystals were transformed into salt crystals even at low temperature.

Based on these observations, an acid-base reaction can be postulated between TPA and the solvent to form the salt: TPA(s)+2NMP(1)→TPA:2NMP(s).

Studies of melting point determinations of NMP-salt crystals indicated that bright and transparent crystals are transformed into opaque and white crystals at 50–60° C. and remained the same until temperature was >300° C. when some visible vapors were evolved, indicating possible sublimation. The same phenomena was observed for salt crystals formed from DMAC.

Experiments in which salt crystals were dried to remove the solvent showed weight loss at about 60% of the original weight which is consistent with the salt formula proposed by earlier workers. In drying tests at temperatures above 120° C., the material turned brown.

Heating salt crystals at temperatures between 8°–100° C with some agitation forms a slurry with a clear liquid (NMP) and white, opaque, hard crystals (TPA). Slurry formation was also observed at higher temperatures.

These observations indicate that salt decomposition occurs at a temperature of 60° C. or higher into TPA and NMP. At temperatures below 50° C., the salt is more stable. Therefore, the salt decomposition reaction can be stated as follows:

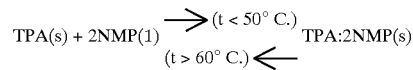

In accordance with the invention, this concept has been used to set crystallization conditions in order to produce true TPA crystals which can stand in water and prevent all the problems related to salt regeneration as mentioned before.

Experiments involving either cooling or flash/cooling of solutions to 60° C. crystallization temperature (instead of 45° C.) have confirmed the salt formation/decomposition mechanism postulated above, by producing true TPA crystals which are not destroyed by water.

Further in accordance with the invention, the solution of an organic solvent (or mixture of organic solvents) saturated with TA and impurities such as 4-carboxybenzaldehyde (4-CBA), p-toluic acid, etc., is fed to a crystallizer maintained at a lower pressure (or under vacuum) to allow the solvent (or solvent mixture) to flash instantaneously in a continuous or batch manner at temperatures maintained above 50° C. to avoid salt formation. Then, the solids (nuclei) generated from solvent flashing are allowed to grow for a certain period of time at the reduced pressure and temperature. It is desirable to subject the saturated solution to a number of solvent flash operations in the same crystallizer or in several crystallizers connected in series, each at a different reduced pressure (or vacuum), to generate higher TA recovery and larger TA crystals. It has been found, surprisingly, that the structure of the crystals produced from this method is not adversely affected by washing with water or other solvents which have significant solubility for the crystallization solvent (or mixture of solvents) or by vacuum drying the crystals to remove solvent. Consequently, it appears that there was no salt formation or at least the salt formation was minimized so that washing with water or other solvent which can dissolve the crystallization solvent or vacuum drying did not change the size and shape of the TA crystals.

Figure 5:
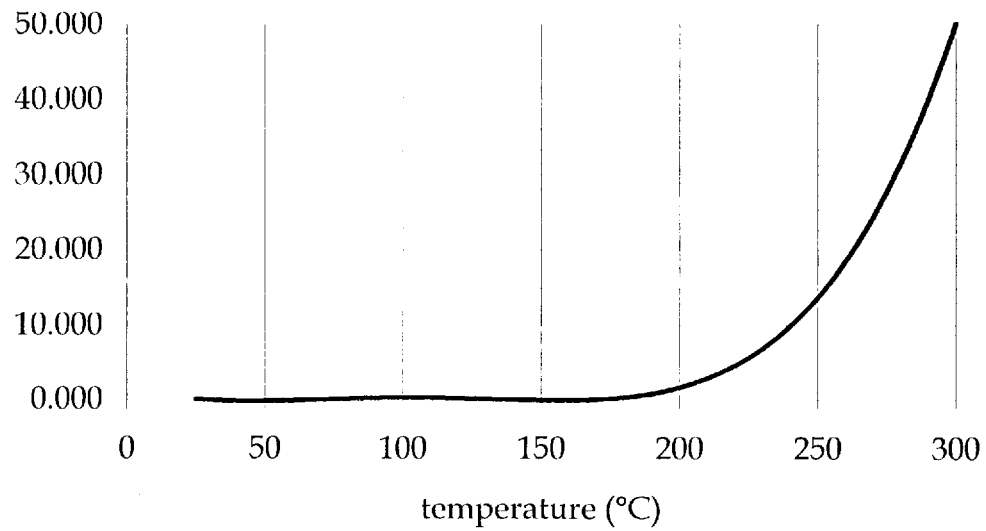
FIG. 5 is a plot of the solubility of TPA in water against temperature with flash points for a certain prior art process indicated.

Flash crystallization is being used commercially for TPA using water as the solvent. This process requires 3–5 flashes to reduce pressure and temperature and achieve a good particle size and distribution (120 microns average). This type of crystallization takes advantage of the shape of the solubility curve to create a high supersaturation condition, especially in the first flash as reported in the prior art and shown in FIG. 5 which is a plot of the solubility of TPA in water against temperature.

Figure 6:
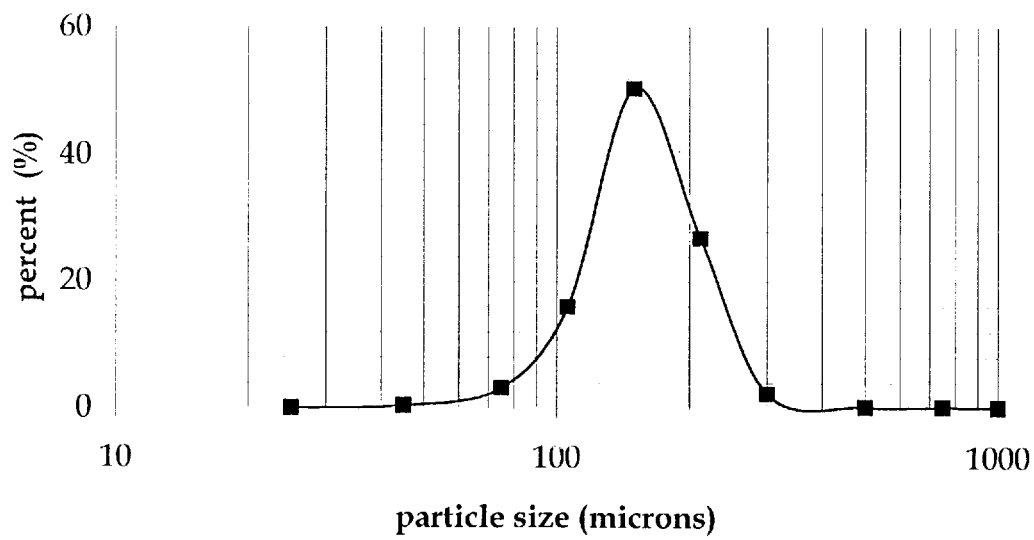
FIG. 6 shows the particle size distribution obtained by a flash process in accordance with the invention.

In contrast to its behavior in water, the solubility curve of TPA in NMP is very flat, but crystal growth rate is higher based on flash crystallization procedures using only 4 flashes: larger crystals are obtained (160–170 microns average). Also, crystals from flash crystallization are larger than those obtained by cooling alone. FIG. 6 shows the particle size distribution obtained by such a flash process.

Figure 7:
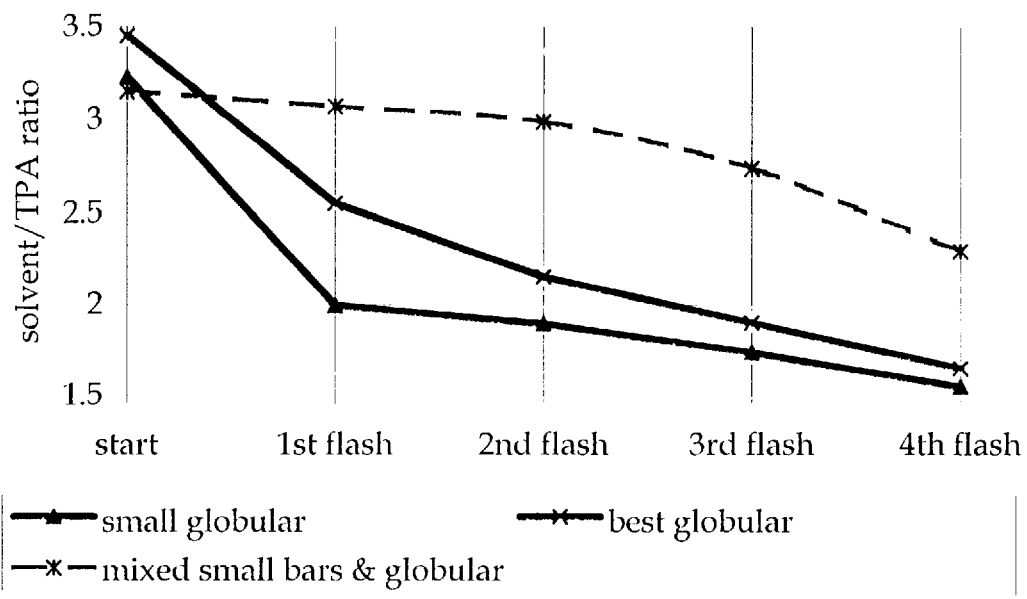
FIG. 7 is a plot of flash profiles for various flashing processes.

Good control of the flash profile (amount of solvent flash-out after each flash) is important to promote the desired particle shape and size. Flash crystallization is the only way to produce globular type crystals which have good filtration rates and wash efficiencies, but if too much solvent is flashed-out in the first two flashes, then small globular crystals are obtained which are somewhat difficult to filter and wash. Selection and control of flash profile thus provides a way to create the desired or optimum supersaturation conditions with respect to crystal shape and size, as is shown in FIG. 7.

Preferably, the flash crystallization method using NMP runs under vacuum, because of the low vapor pressure of the solvent, compared to flash crystallization in acetic acid or water methods that run under pressure. Preferred flash conditions are:

| | |
|---|---|
| 1$^{st}$ flash: | 150 mmHg @ 145–150° C., V/F* = 0.26 |
| 2$^{nd}$ flash: | 80 mmHg @ 120–125° C., V/F = 0.12 |
| 3$^{rd}$ flash: | 40 mmHg @ 110–115° C., V/F = 0.07 |
| 4$^{th}$ flash: | 20 mmHg @ 95–100° C., V/F = 0.07 |

*Amount of solvent flash as a fraction of initial solvent for each flash.

Figure 8:
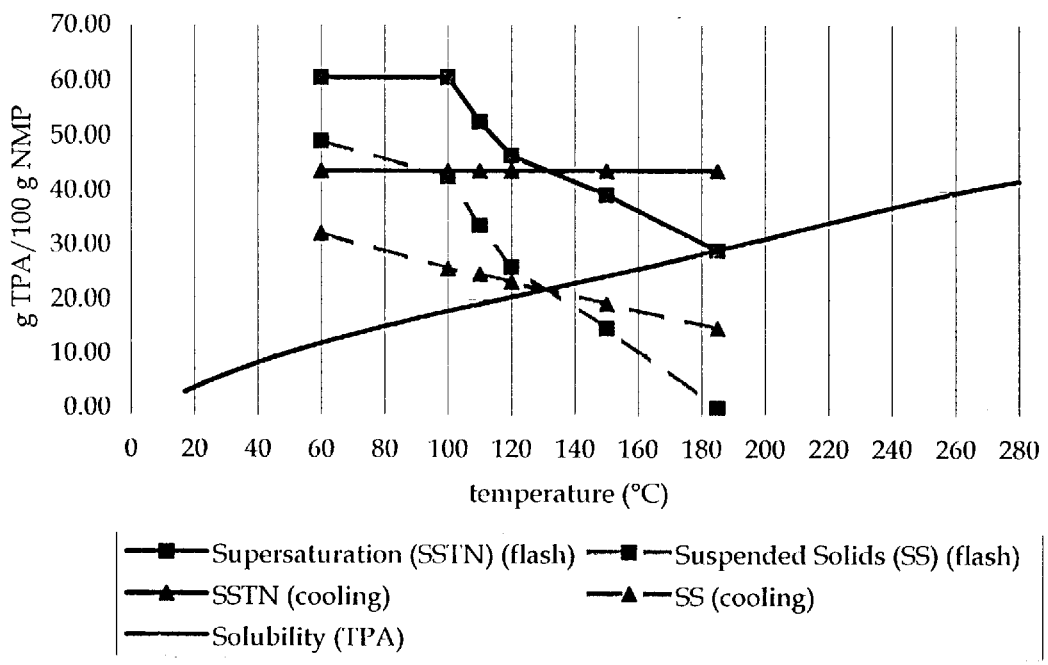
FIG. 8 shows the cooling curves for various processes, both flash and cooling type.

Experiments were done by both cooling or flash crystallization methods to end points at 60° C., making true TPA crystals by both methods, although they are different in shape and size from each other. For flash crystallization, complete dissolution (29 g TPA/100 g NMP @ 185° C.) is preferred at initial conditions, but, for cooling, some seeding is required so initial conditions are preferably 43.7 g TPA/ 100 g NMP @ 185° C. The crystal shapes obtained by cooling were a mixture of bar and globular, but predominantly globular and smaller than those produced by flash, as a result of lower supersaturation conditions achieved at the end of the crystallization step by cooling (31 g TPA/100 g NMP as suspended solids in cooling compared to 49 g TPA/100 g NMP in flash). FIG. 8 shows the cooling curves for various processes, both flash and cooling.

In accordance with the invention, the holding time to allow crystals to grow is a very important factor. A minimum of 15 min. and a maximum of 60 min. is preferred, with an optimum around 30 min. This time is enough to achieve a certain equilibrium between the liquid and solid phases and to minimize plugging problems during filtration.

In summary, these are the results from a number of crystallization tests:

| 4-CBA in crude (%) | FIRST STAGE | SECOND STAGE |
|---|---|---|
| 2–3% | 300–500 ppm (cooling) | 30–50 ppm (cooling) |
| 0.3 | –300 ppm (cooling) | <29 ppm (flash) |
| 0.8 | –250 ppm (cooling) from 200 ppm 4-CBA | <20 ppm (flash) |

As previously mentioned, organic solvents useful in this invention include, but are not limited to, N-methyl pyrrolidone (NMP), N,N-dimethyl acetamide (DMAC), 1,5-dimethyl pyrrolidone, N-methyl piperidone, N-methyl caprolactam, N,N-dimethyl formamide, N-formyl piperidine, N-alkyl-2-pyrrolidone (such as N-ethyl pyrrolidone), N-mercaptoalkyl-2-pyrrolidone (such as N-mercaptoethyl-2-pyrrolidone), N-alkyl-2-thiopyrrolidone (such as N-methyl-2-thiopyrrolidone), and N-hydroxyalkyl-2-pyrrolidone (such as N-hydroxyethyl-2-pyrrolidone).

In order to remove the residual solvent trapped in the crystals from the final TA product, the washed TA crystals are preferably fed to a high temperature soaker where water is used to partially or completely dissolve the TA crystals.

Several attempts to remove residual solvent by vacuum or low temperature drying of salt crystals were done. The results showed 0.5% of residual solvent still remained, apparently because agglomeration of fine particles occurred, trapping some solvent in between particles of the agglomeration.

Soaking at 220° C. in water at different water to TPA ratios demonstrated that residual solvent can be effectively and satisfactorily removed without the need for complete dissolution:

| g TPA/100g water | % dissolution | residual solvent (ppm) |
|---|---|---|
| 5.0 | 80.0 | <20 |
| 4.4 | 90.9 | <20 |
| 6.2 | 64.5 | <25 |

The following examples illustrate the principles and features of the invention.

EXAMPLE 1

Cooling Crystallization 9761 g of NMP was added to a jacketed crystallizer provided with agitation together with 3028 g of TA. This mixture was heated to 180° C. under atmospheric pressure until all of the TA was dissolved.

The mixture was then subjected to surface cooling by circulating a cooling medium through the jacket until a temperature of 45° C. was reached. Then after 15 minutes, the slurry was filtered to separate the solids from the mother liquor, and the cake was washed with room temperature pure NMP to displace all the mother liquor from the cake.

A sample was taken from the cake for observation under a microscope. The crystals had a bar-like shape and a size in the range of 120–150 microns.

In order to remove the solvent from the cake, the cake had to be washed with water or other suitable solvents which have high solubility of the solvent. Hot water at 80° C. was used to wash the cake. However, the bar-like crystals in the cake were completely destroyed by water and changed into fine powders which looked more like precipitates than crystals produced by a crystallization process. These fine precipitates are extremely difficult to wash and handle and the residual solvent removal is complicated.

EXAMPLE 2

Flashing Crystallization

The same sample preparation of NMP and TA as in the previous example was used, except that the mixture was also, prior to the cooling step, subject to a flashing removal of solvent by reducing the pressure from atmospheric to 125 mmHg of vacuum. In this way, some solvent was vaporized out and condensed through a cooler so the temperature of the mixture dropped from 180° C. to 147° C. The amount of solvent flashed out created a super-saturation condition so the TA dissolved in NMP crystallizes into the solid phase.

Although the flashing step is done instantaneously, crystallization of TA requires some time to take place, so the mixture was kept agitated for 30 minutes to form the nuclei and permit them to grow, thus forming a slurry. The slurry was filtered to separate the solids from the liquid phase, washed with pure NMP at room temperature and observed under a microscope. The crystal shape was globular instead of bar-like, as it was when using the previous cooling crystallization method, and very uniform in size but smaller—about 40–60 microns.

Then the cake was washed with hot water at 80° C. and, surprisingly, the globular-like crystals were not affected by water washing (their shape and size were not changed). These globular-like crystals have a very high filtration rate and effectively rinsing them is much easier.

EXAMPLE 3a

Crystal Growth

To promote crystal growth, the experiment, as in the preceding example, was repeated except that 6174 g of NMP and 1952 g of terephthalic acid were used.

Also, the flash pressure was 120 mmHg instead of 125 mmHg and the temperature was 145° C. Then, the mixture was flashed a second time at 40 mmHg, as described in the preceding example, and the temperature dropped to 110° C. Thus, more terephthalic acid crystallized. The crystal shape was globular-like and the size was increased to 60–80 microns.

EXAMPLE 3b

The experiment as in Example 3a was repeated except that 7490 g of NMP and 2325 g of terephthalic acid were used. Also, a different pressure profile was followed and two more flashes were added:

| | |
|---|---|
| first flash: | 150 mmHg @ 154° C. |
| second flash: | 80 mmHg @ 135° C. |
| third flash: | 40 mmHg @ 117° C. |
| fourth flash: | 20 mmHg @ 101° C. |

Observation under a microscope showed that the crystal shape was globular and the size improved significantly. The final sample contained crystals in the range of 120–150 microns.

EXAMPLE 4a and 4b

Flash/Vaporizing Crystallization

The experiment as in Example 3b was repeated except that the temperature of the hot oil circulation through the jacket was kept 5°–10° C. above the crystallizer temperature in a way that some vaporization of the solvent occurred at the same time of the flashing. This procedure resulted in more solvent flashed/vaporized and a lower temperature profile which increases the recovery of the crystals:

| FLASH No. | EXAMPLE 3b | EXAMPLE 4a | EXAMPLE 4b |
|---|---|---|---|
| First | 154° C. | 155° C. | 145° C. |
| | 150 mmHg | 150 mmHg | 150 mmHg |
| | 755 ml of solvent removed by flashing | 1328 ml of solvent removed by flashing | 1660 ml of solvent removed by flashing |
| Second | 135° C. | 135° C. | 130° C. |
| | 80 mmHg | 80 mmHg | 80 mmHg |
| | 696 ml of solvent removed by flashing | 473 ml of solvent removed by flashing | 580 ml of solvent removed by flashing |
| Third | 117° C. | 110° C. | 115° C. |
| | 40 mmHg | 40 mmHg | 40 mmHg |
| | 248 ml of solvent removed by flashing | 110 ml of solvent removed by flashing | 340 ml of solvent removed by flashing |
| Fourth | 101° C. | 90° C. | 95° C. |
| | 20 mmHg | 20 mmHg | 20 mmHg |
| | 135 ml of solvent removed by flashing | 155 ml of solvent removed by flashing | 430 ml of solvent removed by flashing |

When observed under a microscope, the crystals looked globular-like in shape as described for Example 2 above.

EXAMPLE 5

In this example, the 4-CBA rejection characteristics of the flash crystallization method was compared with that of crystallization by cooling alone.

Flash Crystallization

The crystallizer was charged with 31 g TA/100 g solvent. 4-CBA was added to start with a concentration based on solids of around 2%. The mixture was heated to 185° C. and agitated until most of the crystals dissolved. Some crystals may not have dissolved and these became seeds for crystal growth. The oil bath was set to 155° C. The first vacuum (150 mmHg) was pulled to remove around 15–20% of the liquid in about 15 minutes. Next, the flash vacuum was pulled to 80 mmHg and 6–8% of the remaining liquid was removed within 5 minutes. In the third flash, 68% of the solvent was removed with a vacuum of 40 mmHg requiring about 6–7 minutes. In the fourth flash, 12% of the solvent was removed with a vacuum of 20 mmHg requiring about 10–15 minutes. Then the mother liquor was cooled to 50° C. as quickly as possible, taking about 30 minutes. The crystals were then removed from the flask and filtered using a Buchner funnel and side arm flask. About 200 g of 50° C. solvent was then poured over to wash the crystals. The crystals were then put in a pressure filter and dried by passing nitrogen for 30 minutes at 40 psi. The final crystals were analyzed for 4-CBA content, giving a result of 500 ppm.

Cooling Crystallization

The crystallizer was charged with 31 g TA/100 g solvent. 4-CBA was added to start with a concentration based on solids of 2%. The mixture was heated to 185° C. and agitated until most of the crystals dissolved. Some crystals may not have dissolved and these became seeds for crystal growth. Cooling of the mix was started to crystallize the TA from the solution. The cooling rate was 2° C./min to a final temperature of 50° C. The crystals were then removed from the flask and filtered using a Buchner funnel and side arm flask. About 200 g of 50° C. solvent was then poured over to wash the crystals. The crystals were then put in a pressure filter and dried by passing nitrogen for 30 minutes at 40 psi. These final crystals were analyzed for 4-CBA content, giving a result of about 500 ppm.

The experiments show that the flash and cooling crystallization processes have substantially the same rejection capability for 4-CBA.

According to the invention, a preferred embodiment of the process is divided into five sections:

(1) Oxidation Section:

In this section, p-xylene is oxidized according to the following main reactions:

(a) p-xylene+oxygen→terephthalic acid+water (b) p-xylene+oxygen→p-toluic acid+water (c) p-xylene+oxygen→4-carboxybenzaldehyde (4-CBA) +water The oxidizer residence time is approximately five hours. Since the oxidizer effluent will contain up to about 30% TA, mixing in the oxidizer is very important in order to maintain the yield and selectivity, and to prevent fouling and blockages. The initial mixing of the feed streams may be achieved in a static mixer (outside of the oxidizer). Further mixing may be provided by an air sparger and by external circulation. Depending on the thoroughness of the p-xylene washing step at the filter (discussed below), the terephthalic acid (TA) in the solid can vary from between about 55% and about 90+%.

(2) Crystallization Section:

(A) First Crystallization

After filtration, the solids from the oxidizer effluent are mixed with the mother liquor and the solvent wash liquid from the second-stage crystallizer and with additional crystallization solvent. The mixed slurry is dissolved in a slurry tank at a predetermined temperature, preferably at from between about 140° C. and about 200° C. The saturated solution is transferred to a holding tank to remove p-xylene through evaporation. The saturated solution is then fed to a first-stage batch crystallizer to recover purified TA by flash evaporation of solvent at reduced pressure and/or cooling. After the crystallization step, the crystallizer content is then dropped to a product holding tank and is pumped continuously to a filter (or centrifuge) to collect the solids to be recrystallized in the second-stage crystallizer for further purification.

(B) Second Crystallization

The solids generated from the first crystallizer filter are redissolved in a feed dissolver with the crystallization solvent for the second-stage crystallizer at a predetermined condition, such as at a temperature of from between about 140° C. and about 200° C. The saturated solution is pumped to the second-stage crystallizer for crystal growth and recovery, again, by flash evaporation of solvent at reduced pressure and/or cooling. Then, the crystallizer content is dropped to a holding tank for filtration before being sent to the soaker. In the filtration step, the solid (cake) is first washed by the crystallization solvent to displace mother liquor remaining in the cake. The solid is then washed by a low-boiling solvent to displace the crystallization solvent in the cake, soaked at high temperature in water to remove any residual solvent, and subsequently dried to remove the final liquid from the PTA product. The crystallization solvent alternatively can be displaced by drying the solid using a vacuum dryer and subjecting the cake to a soaking process. The soaking process comprises partially or completely dissolving the TA in a solvent, crystallizing the product in water at a high temperature and high pressure to remove residual solvent trapped in the crystals, and recrystallizing, filtering and drying the TA cake.

(3) Mother Liquor/Solvent Recovery Section:

The mother liquor from the first crystallizer filter is transferred to a solvent recovery column to recover the crystallization solvent from the column overhead. The impurities, such as, but not intended to be limited to, p-toluic acid, benzoic acid, 4-carboxybenzaldehyde (4-CBA), and the like, are recovered from the bottom of the column. In order to make sure the column bottom slurry can be transferred back to the oxidizer, a high-boiling diluent is preferably added to the reboiler.

II. Detailed Process Description and Example

The present invention will be described in terms of the production and recovery of terephthalic acid (TA) from the air oxidation of p-xylene in the presence of a solution of components of catalysis in dimethyl terephthalate (DMT) or in benzoic acid solvent system. The oxidizer temperature is preferably between about from 150° C. and about 250° C. and the pressure is from between about 5 and about 30 kg per $cm^2$. Since the oxidizer effluent will contain up to 30% TA, mixing in the oxidizer is very important in order to maintain the yield and selectivity, and to prevent fouling and blockages. The initial mixing of the feed streams may be achieved in a static mixer (outside of the oxidizer). Further mixing may be provided by air sparging and external circulation. In the preferred form of the process manganese acetate and cobalt acetate in aqueous solution are fed to the oxidizer to catalyze the oxidation reactions.

The effluent from the oxidizer at about 160° C. is transferred and filtered via a first filter to separate the solid from mother liquor (filtrate). During filtering, the solid cake is washed with p-xylene which is heated from 30° C. to 100°–150° C. The mother liquor is transferred to a first holding tank. The cake washing liquid is removed separately from the first filter to a second holding tank.

The washed cake is dropped into a first slurry tank to mix with the following streams: (1) NMP or DMAC (selective crystallization solvent) wash liquor (heated from 45 to 100°–150° C.); (2) mother liquor (heated from 50° C. to 100°–150° C.); and (3) NMP or DMAC (heated from 45° C. to 100–150° C.).

When a crude TA from existing or prior oxidation systems is used, the p-xylene wash is not necessary, and the crude TA is dropped into the first slurry tank as described above. Crude TA can contain as much as 2–3% of 4-CBA; thus oxidation conditions may be relaxed, which will result in significantly reduced p-xylene and acetic acid burning losses.

The above mixture is then transferred from the bottom of the first slurry tank to a first dissolver tank. The content in the first dissolver tank is then heated indirectly from 100°–150° C. to 140°–200° C. by a hot oil heating coil in the first dissolver tank. About 75% of the p-xylene and 100% of the sparging nitrogen in the mixture is vaporized from the first dissolver tank and removed. Sparging nitrogen is added to the first dissolver tank to assist the removal of p-xylene. Vapor streams from the first dissolver tank and a crude crystallizer are combined into a stream, condensed by a cooler, and sent to a first storage tank. The bottom effluent from the first dissolver tank is transferred to the crude crystallizer batchwise.

The batch content in the crude crystallizer is cooled from 140°–200° C. to 30°–50° C. by an external cooler, to generate the desired super-saturation for TA crystals to grow. To improve the crystal size distribution and solid recovery, crystal seeding may be helpful. At the conclusion of a batch crystallization cycle, the slurry is dropped into a third holding tank and transferred to a second filter where it is filtered at a continuous rate.

During filtering at the second filter, NMP or DMAC is used to wash the cake in the second filter. The mother liquor plus NMP or DMAC wash are combined to be fed to a crystallization solvent recovery column. The washed cake is dropped into a second dissolver tank where it is mixed with NMP or DMAC to form the super-saturated feed for a pure crystallizer. NMP or DMAC is heated from 45° C. to 140°–200° C. and is fed to the second dissolver tank.

The content of the second dissolver tank is transferred batchwise to the pure crystallizer where the pressure is reduced in the manner described previously and the temperature is reduced from 140°–200° C. to 50°–60° C. to induce TA crystal growth. The cooling to promote super-saturation results from the flashing steps. Again, to improve the crystal size distribution and crystal recovery, crystal seeding may be helpful. At the end of the batch cycle, the slurry is dropped from the pure crystallizer into a feed tank for the third filter.

The slurry is continuously fed to the third filter. The mother liquor from the first filter is transferred to a fourth holding tank. The cake is initially washed with NMP or DMAC at 45° C. to displace the remaining mother liquor from the cake, and then the cake is washed with the low-boiling displacement solvent, such as water, to displace NMP or DMAC from the cake or, alternatively, sent to a vacuum dryer. The NMP or DMAC wash (from a crystallization solvent storage tank) and the displacement solvent are then added to the third filter. The NMP or DMAC wash liquid is sent to the first slurry tank, while the displacement solvent is transferred to a fifth holding tank.

The washed cake from the third filter is passed through a wash column or multistage contactor and counter-current water is added to remove the crystallization solvent. The slurry from the wash column or contactor is then fed to the soaker where the temperature is raised to from between about 150°–250° C. to remove trapped solvent from the crystals. The slurry is finally filtered and dropped to a product dryer where water (moisture) in the cake is removed by heating and purging with a counter-current flow of heated nitrogen. The dried PTA product is removed from the dryer and is stored in the product bin.

The bottom stream from the fifth holding tank (mixture of NMP and displacement solvent), together with the liquid from the wash column or multi-stage contactor, is transferred through a heater (to heat the stream from 25° C. to 80°–120° C.) to a displacement solvent evaporator. The displacement solvent vapor from the overhead of the displacement solvent evaporator is condensed and sent to the displacement solvent tank. The bottom stream from the displacement solvent evaporator is split into two streams: one stream to the vent pot and a second stream to the crystallization solvent tank.

The mother liquor and NMP or DMAC wash from the second filter are transferred to the crystallization solvent tank and then are fed to the NMP or DMAC recovery column. This stream is heated from 15°–45° C. to 130°–170° C. before entering the recovery column. The overhead vapor is condensed and sent to a condensate pot. A part of the condensate at 160°–220° C. is returned to the recovery column as the reflux. The rest of the overhead product from recovery column is sent to a crystallization solvent check tank. From the crystallization solvent check tank, the regenerated NMP or DMAC is pumped to a NMP or DMAC storage tank.

In order to make sure the slurry in the recovery column reboiler can be transferred back to the oxidizer, high-boiling diluent, such as benzoic acid or DMT, is added to the reboiler. The slurry plus the high-boiling diluent is withdrawn from the bottom of the recovery column and is sent back to the oxidizer.

Figure 9:
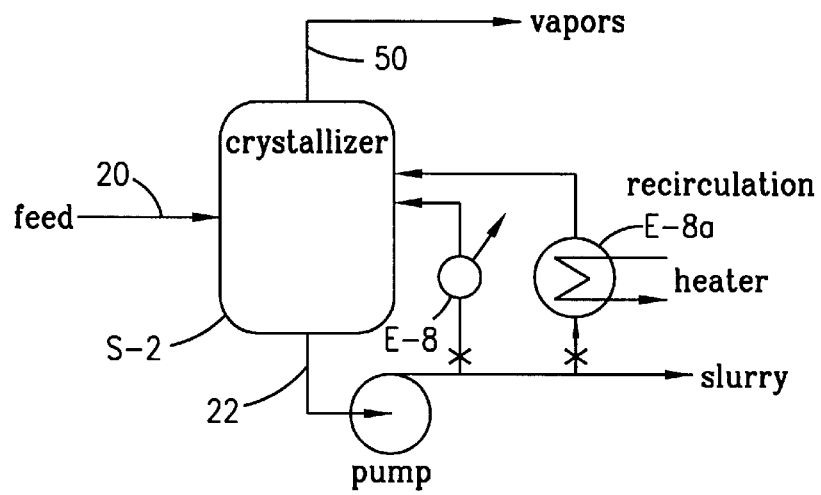
FIG. 9 is a simplified elevational diagram of a crystallizer which may be used in the practice of the invention.

In FIG. 9, there is shown an arrangement of a crystallizer S-2 useful for the practice of the embodiment of the invention in which heat is added to the crystallizing acid mixture during the times when the pressure is being reduced to flash solvent. As shown in FIG. 3, crystallizer S-2 is there provided with both a cooling recirculation circuit with exchanger E-8, and a heating recirculation circuit with heater E-8$a$. Heat is applied to the mixture by heater E-8$a$ during flashing, and cooling is applied to the mixture at other times by exchanger E-8. Flashed solvent (e.g. NMP or DMAC) is removed through line 50 for recycling to the recovery column, and the pressure reduction vacuum is also applied to the crystallizer through line 50.

Figure 10:
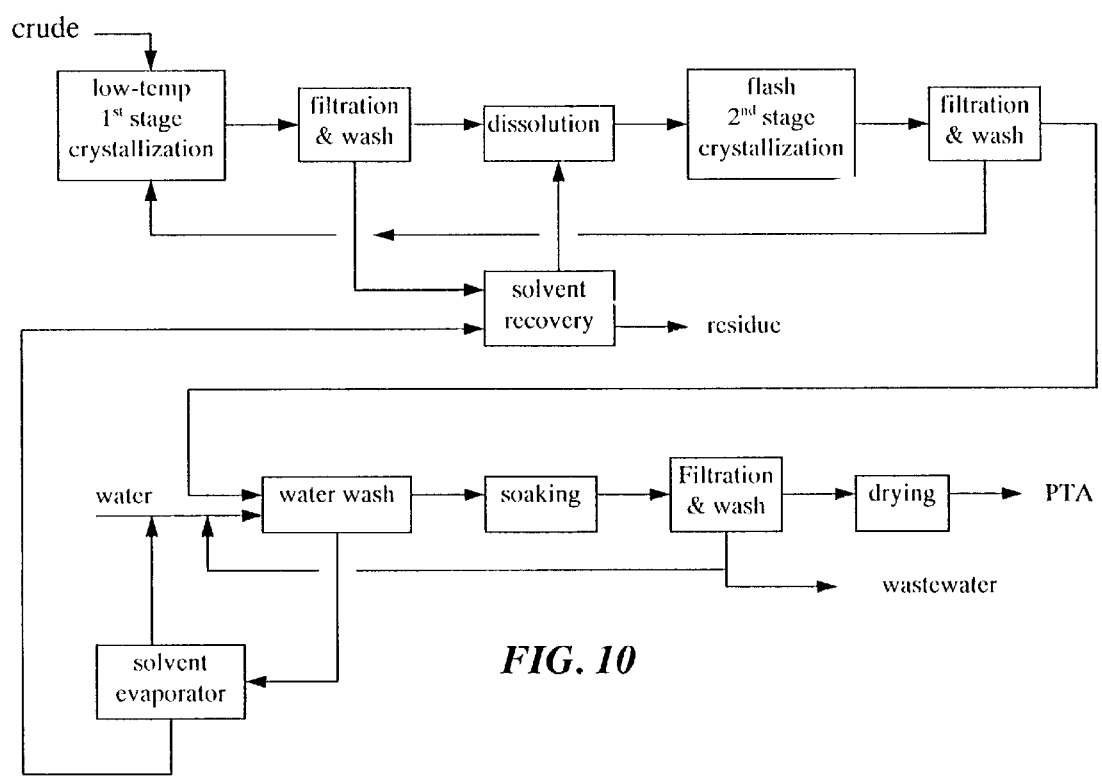
FIG. 10 is a process block diagram for a preferred process of the invention.

FIG. 10 is a process block diagram for a preferred purification process of the invention based on the several considerations discussed herein above.

This new configuration using soaking instead of water recrystallization reduces capital cost and energy requirements.

Another improvement is to use single stage flash crystallization if 4-CBA in the crude is about 0.3%–0.8% and 4-CBA requirements in the final product are between 200–400 ppm.

Although preferred embodiments of the method and apparatus of the present invention have been illustrated in the accompanying Drawings and described in the foregoing Detailed Description, it will be understood that the invention is not limited to the embodiments disclosed, but is capable of numerous rearrangements, modifications and substitutions without departing from the spirit of the invention as set forth and defined by the following claims.

What is claimed is:

1. A method for purifying crude terephthalic acid from a liquid dispersion thereof also containing impurities selected from unreacted starting materials, solvents, products of side reactions and/or other undesired materials comprising:

filtering said dispersion to form a crude terephthalic acid filter cake;

dissolving said filter cake in a selective crystallization solvent at a temperature between about 50° C. and about 250° C. to form a solution;

crystallizing purified terephthalic acid from said solution by reducing the temperature and/or pressure thereof;

separating said crystallized purified terephthalic acid from said solution;

redissolving said separated purified terephthalic acid in a selective crystallization solvent to form a second solution;

crystallizing second stage purified terephthalic acid from said second solution by reducing the temperature and pressure sufficient to flash evaporate solvent from said terephthalic acid of said second solution but without cooling said solution below about 50° C.;

separating said second stage purified terephthalic acid from said second solution;

washing said separated second stage purified terephthalic acid with water;

soaking said washed separated second stage purified terephthalic acid with water at a temperature between about 150° C. and about 300° C.; and filtering and drying said water soaked second stage purified terephthalic acid.

2. A method in accordance with claim 1 in which said soaking with water is done between about 180° C. and about 250° C.

3. A method in accordance with claim 1 in which said second solution is held from about 15 to about 60 minutes following said reduction of temperature and prior to separating said second stage purified terephthalic acid therefrom.

4. A method in accordance with claim 3 in which said second solution is held between about 20 to about 40 minutes.

5. A method in accordance with claim 1 in which said washing of purified terephthalic acid is done between one and three times.

6. A method in accordance with claim 1 in which said reducing the temperature and pressure to flash evaporate solvent is performed stage-wise, in from two to six stages.

7. A method in accordance with claim 6 in which said reducing of the temperature and pressure is done in two to four stages.

8. A method in accordance with claim 6 in which the proportion of solvent flash evaporated in the first evaporation stage is restricted to increase final crystal size.

9. A method for purifying crude terephthalic acid from a liquid dispersion thereof also containing impurities selected from unreacted starting materials, solvents, products of side reactions and/or other undesired materials comprising:
   preparing first stage purified terephthalic acid from said crude terephthalic acid;
   redissolving said first stage purified terephthalic acid in a selective crystallization solvent to form a solution;
   crystallizing second stage purified terephthalic acid from said second solution by reducing the temperature and pressure sufficient to flash evaporate solvent from said terephthalic acid of said second solution but without cooling said solution below about 50° C.;
   separating said second stage purified terephthalic acid from said second solution;
   washing said separated second stage purified terephthalic acid with water;
   soaking said washed separated second stage purified terephthalic acid with water at a temperature between about 150° C. and about 300° C.; and
   filtering and drying said water soaked second stage purified terephthalic acid.

10. A method in accordance with claim 9 in which said soaking with water is done between about 180° C. and about 250° C.

11. A method in accordance with claim 9 in which said second solution is held from about 15 to about 60 minutes following said reduction of temperature and prior to separating said second stage purified terephthalic acid therefrom.

12. A method in accordance with claim 11 in which said second solution is held between about 20 to about 40 minutes.

13. A method in accordance with claim 9 in which said washing of purified terephthalic acid is done between one and three times.

14. A method in accordance with claim 9 in which said reducing the temperature and pressure to flash evaporate solvent is performed stage-wise, in from two to six stages.

15. A method in accordance with claim 14 in which said reducing of the temperature and pressure is done in two to four stages.

16. A method in accordance with claim 14 in which the proportion of solvent flash evaporated in the first evaporation stage is restricted to increase final crystal size.

17. A method for purifying crude terephthalic acid from a liquid dispersion thereof also containing impurities selected from unreacted starting materials, solvents, products of side reactions and/or other undesired materials comprising:
   filtering said dispersion to form a crude terephthalic acid filter cake;
   dissolving said filter cake in a selective crystallization solvent at a temperature between about 50° C. and about 250° C. to form a solution;
   crystallizing purified terephthalic acid from said solution by reducing the temperature and/or pressure of said solution but not below about 50° C.;
   separating said crystallized purified terephthalic acid from said solution;
   washing said separated purified terephthalic acid with water;
   soaking said washed separated purified terephthalic acid with water at a temperature between about 150° C. and about 300° C.; and
   filtering and drying said water soaked purified terephthalic acid.

18. A method in accordance with claim 17 in which said soaking with water is done between about 180° C. and about 250° C.

19. A method in accordance with claim 17 in which said second solution is held from about 15 to about 60 minutes following said reduction of temperature and prior to separating said second stage purified terephthalic acid therefrom.

20. A method in accordance with claim 19 in which said second solution is held between about 20 to about 40 minutes.

21. A method in accordance with claim 17 in which said washing of purified terephthalic acid is done between one and three times.

22. A method in accordance with claim 17 in which said reducing the temperature and pressure to flash evaporate solvent is performed stage-wise, in from two to six stages.

23. A method in accordance with claim 22 in which said reducing of the temperature and pressure is done in two to four stages.

24. A method in accordance with claim 22 in which the proportion of solvent flash evaporated in the first evaporation stage is restricted to increase final crystal size.

25. A method for purifying crude terephthalic acid from a liquid dispersion thereof also containing impurities selected from unreacted starting materials, solvents, products of side reactions and/or other undesired materials comprising:
   filtering said dispersion to form a crude terephthalic acid filter cake;
   dissolving said filter cake in a selective crystallization solvent at a temperature between about 50° C. and about 250° C. to form a solution;
   crystallizing purified terephthalic acid from said solution by reducing the temperature and/or pressure thereof;
   separating said crystallized purified terephthalic acid from said solution;
   redissolving said separated purified terephthalic acid in a selective crystallization solvent to form a second solution;
   crystallizing second stage purified terephthalic acid from said second solution by reducing the temperature and pressure sufficient to flash evaporate solvent from said terephthalic acid of said second solution but without cooling said solution below about 50° C.; and
   separating said second stage purified terephthalic acid from said second solution.

26. A method in accordance with claim 25 in which said second solution is held from about 15 to about 60 minutes following said reduction of temperature and prior to separating said second stage purified terephthalic acid therefrom.

27. A method in accordance with claim 26 in which said second solution is held between about 20 to about 40 minutes.

28. A method in accordance with claim 25 in which said washing of purified terephthalic acid is done between one and three times.

29. A method in accordance with claim 25 in which said reducing the temperature and pressure to flash evaporate solvent is performed stage-wise, in from two to six stages.

30. A method in accordance with claim 29 in which said reducing of the temperature and pressure is done in two to four stages.

31. A method in accordance with claim 29 in which the proportion of solvent flash evaporated in the first evaporation stage is restricted to increase final crystal size.

* * * * *